(12) United States Patent
Samady et al.

(10) Patent No.: US 11,813,104 B2
(45) Date of Patent: Nov. 14, 2023

(54) METHODS AND SYSTEMS FOR DETERMINING HEMODYNAMIC INFORMATION FOR ONE OR MORE ARTERIAL SEGMENTS

(71) Applicant: EMORY UNIVERSITY, Atlanta, GA (US)

(72) Inventors: Habib Samady, Atlanta, GA (US); Alessandro Veneziani, Decatur, GA (US); Don Giddens, Hilton Head Island, SC (US); David Molony, Atlanta, GA (US); Adrien Lefieux, Decatur, GA (US); Alexander Fuller Viguerie, Atlanta, GA (US)

(73) Assignee: Emory University, Atlanta, GA (US)

( * ) Notice: Subject to any disclaimer, the term of this patent is extended or adjusted under 35 U.S.C. 154(b) by 218 days.

(21) Appl. No.: 16/753,926

(22) PCT Filed: Oct. 8, 2018

(86) PCT No.: PCT/US2018/054802
§ 371 (c)(1),
(2) Date: Apr. 6, 2020

(87) PCT Pub. No.: WO2019/071249
PCT Pub. Date: Apr. 11, 2019

(65) Prior Publication Data
US 2020/0352536 A1    Nov. 12, 2020

Related U.S. Application Data

(60) Provisional application No. 62/569,269, filed on Oct. 6, 2017.

(51) Int. Cl.
*A61B 6/00* (2006.01)
*A61B 6/03* (2006.01)
(Continued)

(52) U.S. Cl.
CPC .............. *A61B 6/507* (2013.01); *A61B 6/032* (2013.01); *A61B 6/463* (2013.01); *A61B 6/466* (2013.01);
(Continued)

(58) Field of Classification Search
CPC ......... A61B 6/507; A61B 6/032; A61B 6/463; A61B 6/466; A61B 6/504; A61B 5/0066;
(Continued)

(56) References Cited

U.S. PATENT DOCUMENTS 6,236,878 B1   5/2001   Taylor et al.
7,739,090 B2   6/2010   Charbel et al.
(Continued)

FOREIGN PATENT DOCUMENTS

CN    106537392 A    3/2017
JP    2014100249 A   6/2014
(Continued)

OTHER PUBLICATIONS

International Search Report and Written Opinion for International Application No. PCT/US2018/054802 dated Dec. 10, 2018, 11 pages.
(Continued)

*Primary Examiner* — Yi-Shan Yang
*Assistant Examiner* — Neshat Baset
(74) *Attorney, Agent, or Firm* — Meunier Carlin & Curfman LLC

(57) ABSTRACT

The systems and methods can accurately and efficiently determine boundary conditions for an arterial segment and thereby efficiently determine hemodynamic information for that segment. The method may include receiving medical image data of a patient. The method may further include generating a geometrical representation of the one or more arterial segments from the medical image data. The method
(Continued)

may further include determining boundaries and geometry data for each arterial segment. The method may further include determining boundary conditions for the inflow boundary and each outflow boundary. The boundary conditions for each outflow boundary may be determined using an outflow distribution parameter. The outflow distribution parameter may be determined using the geometry data for one or more of the one or more outflow boundaries, stored hemodynamic data, or a combination thereof. The method may further include determining flow field for each arterial segment and determining hemodynamic information.

20 Claims, 10 Drawing Sheets

(51) Int. Cl.
  *G06T 7/00* (2017.01)
  *G06T 7/12* (2017.01)
  *G06T 7/60* (2017.01)
  *G06T 17/20* (2006.01)
(52) U.S. Cl.
  CPC ............ *A61B 6/504* (2013.01); *G06T 7/0012* (2013.01); *G06T 7/12* (2017.01); *G06T 7/60* (2013.01); *G06T 17/20* (2013.01); *G06T 2207/30104* (2013.01)
(58) Field of Classification Search
  CPC . A61B 5/055; A61B 2034/105; A61B 5/0261; A61B 5/0263; A61B 5/02007; A61B 5/02108; A61B 6/5217; A61B 8/0891; A61B 8/483; A61B 8/5223; A61B 8/466; A61B 5/02028; G06T 7/0012; G06T 7/12; G06T 7/60; G06T 17/20; G06T 2207/30104; G16H 50/50; G16H 30/40; G06V 40/15; G06V 2201/03
  See application file for complete search history.

(56) References Cited

U.S. PATENT DOCUMENTS

| | | | |
|---|---|---|---|
| 7,929,148 B2 | 4/2011 | Kemp | |
| 7,930,014 B2 | 4/2011 | Huennekens et al. | |
| 8,157,742 B2 | 4/2012 | Taylor | |
| 8,249,815 B2 | 8/2012 | Taylor | |
| 8,311,747 B2 | 11/2012 | Taylor | |
| 8,311,748 B2 | 11/2012 | Taylor et al. | |
| 8,311,750 B2 | 11/2012 | Taylor | |
| 8,315,812 B2 | 11/2012 | Taylor | |
| 8,315,813 B2 | 11/2012 | Taylor et al. | |
| 8,315,814 B2 | 11/2012 | Taylor et al. | |
| 8,318,414 B2 | 11/2012 | Dancu et al. | |
| 8,321,150 B2 | 11/2012 | Taylor | |
| 8,386,188 B2 | 2/2013 | Taylor et al. | |
| 8,449,465 B2 | 5/2013 | Nair et al. | |
| 8,491,567 B2 | 7/2013 | Magnin et al. | |
| 8,496,594 B2 | 7/2013 | Taylor et al. | |
| 8,523,779 B2 | 9/2013 | Taylor et al. | |
| 8,531,428 B2 | 9/2013 | Glynn et al. | |
| 8,548,778 B1 | 10/2013 | Hart et al. | |
| 8,594,950 B2 | 11/2013 | Taylor | |
| 8,606,530 B2 | 12/2013 | Taylor | |
| 8,630,812 B2 | 1/2014 | Taylor | |
| 8,681,116 B2 | 3/2014 | Merritt et al. | |
| 8,706,457 B2 | 4/2014 | Hart et al. | |
| 8,734,356 B2 | 5/2014 | Taylor | |
| 8,734,357 B2 | 5/2014 | Taylor | |
| 8,754,865 B2 | 6/2014 | Merritt et al. | |
| 8,768,669 B1 | 7/2014 | Hart et al. | |
| 8,768,670 B1 | 7/2014 | Hart et al. | |
| 8,797,155 B2 | 8/2014 | Huennekens et al. | |
| 8,803,837 B2 | 8/2014 | Glynn et al. | |
| 8,812,245 B2 | 8/2014 | Taylor | |
| 8,812,246 B2 | 8/2014 | Taylor et al. | |
| 8,824,752 B1 | 9/2014 | Fonte et al. | |
| 8,831,314 B1 | 9/2014 | Fonte et al. | |
| 8,831,315 B1 | 9/2014 | Fonte et al. | |
| 8,837,860 B1 | 9/2014 | Grady et al. | |
| 8,855,984 B2 | 10/2014 | Hart et al. | |
| 8,861,820 B2 | 10/2014 | Fonte et al. | |
| 8,871,461 B2 | 10/2014 | Blackman et al. | |
| 8,914,264 B1 | 12/2014 | Hart et al. | |
| 8,917,925 B1 | 12/2014 | Grady et al. | |
| 8,923,631 B2 | 12/2014 | Spencer | |
| 8,936,553 B2 | 1/2015 | Stigall et al. | |
| 8,958,623 B1 | 2/2015 | Grady et al. | |
| 8,958,863 B2 | 2/2015 | Huennekens et al. | |
| 8,977,336 B2 | 3/2015 | Huennekens et al. | |
| 9,002,690 B2 | 4/2015 | Hart et al. | |
| 9,008,392 B1 | 4/2015 | Bai et al. | |
| 9,008,405 B2 | 4/2015 | Fonte et al. | |
| 9,042,613 B2 | 5/2015 | Spilker et al. | |
| 9,043,190 B2 | 5/2015 | Grady et al. | |
| 9,043,191 B2 | 5/2015 | Grady et al. | |
| RE45,534 E | 6/2015 | Huennekens et al. | |
| 9,055,921 B2 | 6/2015 | Nair et al. | |
| 9,058,692 B1 | 6/2015 | Grady et al. | |
| 9,063,634 B2 | 6/2015 | Hart et al. | |
| 9,063,635 B2 | 6/2015 | Hart et al. | |
| 9,070,214 B1 | 6/2015 | Grady et al. | |
| 9,078,564 B2 | 7/2015 | Taylor et al. | |
| 9,081,721 B1 | 7/2015 | Grady et al. | |
| 9,081,882 B2 | 7/2015 | Taylor et al. | |
| 9,087,147 B1 | 7/2015 | Fonte et al. | |
| 9,121,926 B2 | 9/2015 | Nair et al. | |
| 9,135,699 B2 | 9/2015 | Ralovich et al. | |
| 9,144,417 B2 | 9/2015 | Glynn et al. | |
| 9,149,197 B2 | 10/2015 | Taylor et al. | |
| 9,152,757 B2 | 10/2015 | Taylor et al. | |
| 9,152,761 B2 | 10/2015 | Bhatia et al. | |
| 9,153,047 B1 | 10/2015 | Grady et al. | |
| 9,155,512 B2 | 10/2015 | Choi et al. | |
| 9,159,159 B2 | 10/2015 | Bai et al. | |
| 9,167,974 B2 | 10/2015 | Taylor | |
| 9,168,012 B2 | 10/2015 | Hart et al. | |
| 9,189,600 B2 | 11/2015 | Spilker et al. | |
| 9,195,800 B2 | 11/2015 | Grady et al. | |
| 9,195,801 B1 | 11/2015 | Sankaran et al. | |
| 9,202,010 B2 | 12/2015 | Taylor et al. | |
| 9,220,418 B2 | 12/2015 | Choi et al. | |
| 9,220,419 B2 | 12/2015 | Choi et al. | |
| 9,226,672 B2 | 1/2016 | Taylor et al. | |
| 9,235,679 B2 | 1/2016 | Taylor et al. | |
| 9,239,905 B1 | 1/2016 | Sankaran et al. | |
| 9,262,581 B2 | 2/2016 | Kim et al. | |
| 9,268,902 B2 | 2/2016 | Taylor et al. | |
| 9,271,657 B2 | 3/2016 | Taylor et al. | |
| 9,280,639 B2 | 3/2016 | Sankaran et al. | |
| 9,292,659 B1 | 3/2016 | Grady et al. | |
| 9,292,918 B2 | 3/2016 | Zagrodsky et al. | |
| 9,295,447 B2 | 3/2016 | Shah | |
| 9,304,982 B2 | 4/2016 | Grady et al. | |
| 9,307,926 B2 | 4/2016 | Begin et al. | |
| 9,330,233 B2 | 5/2016 | Bhatia et al. | |
| 9,336,354 B1 | 5/2016 | Sankaran et al. | |
| 9,339,200 B2 | 5/2016 | Fonte et al. | |
| 9,339,348 B2 | 5/2016 | Davies et al. | |
| 9,349,178 B1* | 5/2016 | Itu .................... G06V 10/42 |
| 9,378,580 B2 | 6/2016 | Grady et al. | |
| 9,386,933 B2 | 7/2016 | Grady et al. | |
| 9,390,224 B2 | 7/2016 | Choi et al. | |
| 9,390,232 B2 | 7/2016 | Taylor et al. | |
| 9,424,395 B2 | 8/2016 | Sankaran et al. | |
| 9,424,682 B2 | 8/2016 | Bai et al. | |
| 9,449,145 B2 | 9/2016 | Sankaran et al. | |
| 9,449,146 B2 | 9/2016 | Spilker et al. | |
| 9,449,147 B2 | 9/2016 | Taylor et al. | |
| 9,501,622 B2 | 11/2016 | Sankaran et al. | |
| 9,514,530 B2 | 12/2016 | Grady et al. | |
| 9,517,040 B2 | 12/2016 | Hart et al. | |

(56) References Cited

U.S. PATENT DOCUMENTS

| | | |
|---|---|---|
| 9,585,623 B2 | 3/2017 | Fonte et al. |
| 9,585,723 B2 | 3/2017 | Taylor |
| 9,589,349 B2 | 3/2017 | Grady et al. |
| 9,594,876 B2 | 3/2017 | Sankaran et al. |
| 9,607,130 B2 | 3/2017 | Grady et al. |
| 9,607,386 B2 | 3/2017 | Grady et al. |
| 9,613,186 B2 | 4/2017 | Fonte et al. |
| 9,649,171 B2 | 5/2017 | Sankaran et al. |
| 9,659,375 B2 | 5/2017 | Zagrodsky et al. |
| 9,668,700 B2 | 6/2017 | Taylor et al. |
| 9,672,615 B2 | 6/2017 | Fonte et al. |
| 9,675,301 B2 | 6/2017 | Fonte et al. |
| 9,679,374 B2 | 6/2017 | Choi et al. |
| 9,697,330 B2 | 7/2017 | Taylor |
| 9,706,925 B2 | 7/2017 | Taylor |
| 9,743,835 B2 | 8/2017 | Taylor |
| 9,754,082 B2 | 9/2017 | Taylor et al. |
| 9,770,303 B2 | 9/2017 | Choi et al. |
| 9,773,219 B2 | 9/2017 | Sankaran et al. |
| 2006/0223047 A1 | 10/2006 | Dancu et al. |
| 2006/0235669 A1 | 10/2006 | Charbel et al. |
| 2011/0142316 A1 | 6/2011 | Wang et al. |
| 2011/0059480 A1 | 10/2011 | Blackman et al. |
| 2013/0132054 A1 | 5/2013 | Sharma et al. |
| 2013/0243294 A1 | 9/2013 | Ralovich et al. |
| 2014/0058715 A1 | 2/2014 | Sharma et al. |
| 2014/0200867 A1 | 7/2014 | Lavi et al. |
| 2014/0379318 A1 | 12/2014 | Spilker et al. |
| 2015/0164342 A1* | 6/2015 | Choi .................... A61B 5/7275 600/407 |
| 2015/0238121 A1 | 8/2015 | Tu et al. |
| 2015/0245776 A1 | 9/2015 | Hirohata et al. |
| 2015/0265162 A1 | 9/2015 | Lavi et al. |
| 2015/0324962 A1 | 11/2015 | Itu et al. |
| 2015/0335304 A1 | 11/2015 | Lavi et al. |
| 2015/0342551 A1 | 12/2015 | Lavi et al. |
| 2016/0247279 A1 | 8/2016 | Lavi et al. |
| 2017/0046834 A1 | 2/2017 | Itu et al. |
| 2017/0220760 A1 | 8/2017 | Fonte |
| 2017/0245821 A1 | 8/2017 | Itu et al. |
| 2017/0258431 A1 | 9/2017 | Klingenbeck et al. |
| 2017/0281018 A1* | 10/2017 | Kramer .................. G16H 50/50 |

FOREIGN PATENT DOCUMENTS

| | | |
|---|---|---|
| JP | 2014534889 A | 12/2014 |
| WO | 2006010609 A2 | 2/2006 |
| WO | WO 2006010609 A2 | 2/2006 |
| WO | 2017047820 A1 | 3/2017 |

OTHER PUBLICATIONS

Groen, "Atherosclerotic plaque and shear stress in cartoid arteries," The Netherlands Heart Institute, Nov. 2010.

Xiao, et al., "A systematic comparison between 1-D and 3-D hemodynamics in compliant arterial models," International Journal for Numerical Methods in Biomedical Engineering, 2014, 30: 204-231.

Tesche et al., Coronary CT Angiography-derived Fractional Flow Reserve, Radiology, vol. 285, No. 1, 2017, pp. 17-33.

Extended European Search Report issued in EP 18864098.1, dated Apr. 21, 2021.

English translation of Japanese Office Action issued in JP2020-519335, dated Sep. 13, 2022.

English translation of Japanese Office Action issued in JP2020-519335, dated Feb. 14, 2023.

English translation of Chinese Office Action and Search Report issued in CN201880063964.7, dated Feb. 28, 2023.

Groen, "Atherosclerotic Plaque and Shear Stress in Cartoid Arteries", The Netherlands Heart 21-23, 30-32 Institute, Nov. 10, 2010.

Tesche et al., "Coronary CT Anglography-Derived Fractional Flow Reserve", Radiology, vol. 285, No. 1, pp. 17-33, Oct. 2017.

Xiao et al., "A Systematic Comparison Between 1-D and 3-D Hemodynamics in Compliant Arterial Models", International Journal for Numerical Methods in Biomedical Engineering, vol. 30, pp. 204-231, Feb. 2014.

* cited by examiner

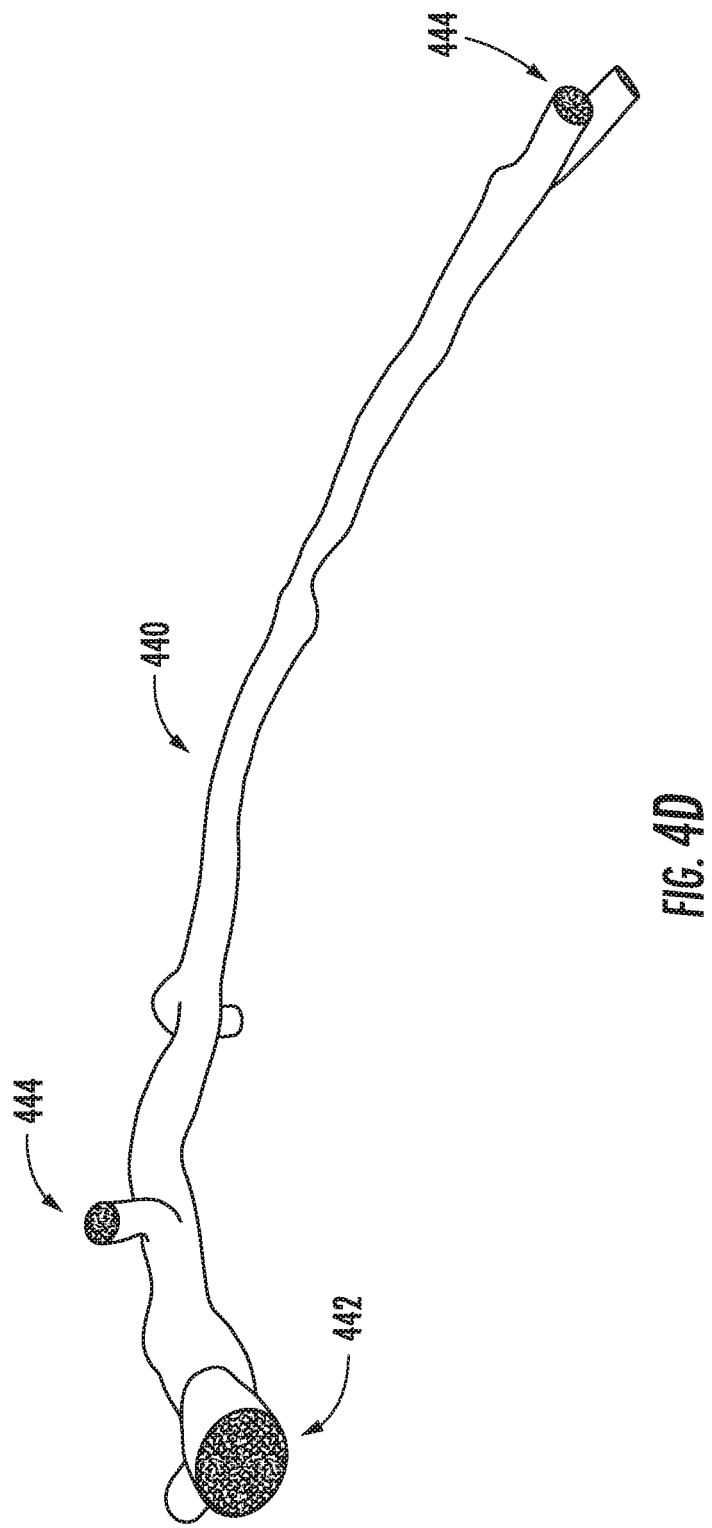

METHODS AND SYSTEMS FOR DETERMINING HEMODYNAMIC INFORMATION FOR ONE OR MORE ARTERIAL SEGMENTS

CROSS-REFERENCE TO RELATED APPLICATIONS

This application is a national phase application of PCT US2018/054802, filed Oct. 8, 2018, which claims benefit of U.S. Provisional Application No. 62/569,269, filed Oct. 6, 2017, which is hereby incorporated herein by reference in its entirety.

BACKGROUND

Coronary heart disease (CHD) is the most common cause of death in the U.S. CHD results from atherosclerosis that can progress and lead to ischemia and angina. Angiographic anatomical findings, and increasingly fractional flow reserve (FFR), have been used as a decisive tool to determine whether there is a need for more invasive procedures, for example, stent placement or coronary artery bypass graft (CABG) surgery, to improve flow across obstructive lesions. FFR can currently be measured invasively, for example, with a pressure wire. Such intervention can be risky and costly to the patient. Or in the alternative, FFR can be computed noninvasively from medical images using the only FDA approved service. However, that service uses a central facility requiring a supercomputer power and therefore needs considerable time to process those images. Therefore, current methods can be costly, inefficient and risky to a patient, and therefore negatively affect the quality of care, the patient experience, and the cost of health care delivery.

SUMMARY

Thus, there is need for systems and methods that provide a fast and accurate determination of hemodynamic information.

The disclosure relates to systems and methods that can accurately determine boundary conditions for a geometrical representation of one or more segments using an outflow distribution parameter and thereby determine boundary conditions in near real-time (e.g., relatively short time). Using the outflow distribution parameter, the systems and methods can determine flow field information and hemodynamic information for each segment in near real-time. Thus, the systems and methods can provide a practitioner with accurate and cost-effective hemodynamic information of a patient, enabling the practitioner to make point of care clinical decisions, thereby improving the patient's healthcare quality and experience.

In some embodiments, the methods may include a computer-implemented method of determining hemodynamic information for a patient. The method may include receiving medical image data of a patient acquired by a medical image acquisition device. The medical image data may include one or more arterial segments and surrounding area. The method may include generating a geometrical representation of the one or more arterial segments from the medical image data. The method may include determining boundaries and geometry data for each arterial segment. The boundaries may include an inflow boundary and one or more outflow boundaries. In some embodiments, the inflow boundary and the one or more outflow boundaries may correspond to a cross-section of each arterial segment. The geometry data may include a radius for the inflow boundary and a radius for each outflow boundary. The method may include determining one or more boundary conditions for the geometrical representation. The one or more boundary conditions may include an inflow boundary condition for the inflow boundary and an outflow boundary condition for each outflow boundary. The outflow boundary condition for each outflow boundary may be determined using an outflow distribution parameter. The outflow distribution parameter may be determined using the geometry data for one or more of the one or more outflow boundaries, stored hemodynamic data, or a combination thereof. The method may further include determining a flow field for each arterial segment using the geometrical representation, one or more of the boundary conditions, and pressure data; and determining hemodynamic information using one or more of the boundary conditions, the flow field, and pressure data for the patient.

In some embodiments, the method may further include displaying the generated geometrical representation and/or the hemodynamic information on a user interface. In some embodiments, the method may further include receiving information regarding a position of a virtual stent disposed along one or more segments of the geometrical representation displayed on the user interface; and generating an updated geometrical representation and/or hemodynamic information.

In some embodiments, the systems may include a system for determining hemodynamic information for a patient. The system may include at least one processor and a memory. The processor may be configured to cause obtaining medical image data of a patient acquired by a medical image acquisition device. The medical image data may include one or more arterial segments and surrounding area. The processor may be configured to cause generating a geometrical representation of the one or more arterial segments from the medical image data. The processor may be configured to cause determining boundaries and geometry data for each arterial segment. The boundaries may include an inflow boundary and one or more outflow boundaries. The inflow boundary and the one or more outflow boundaries may correspond to a cross-section of each arterial segment. The geometry data may include a radius for the inflow boundary and for each outflow boundary. In some embodiments, the processor may be configured to cause determining one or more boundary conditions for the geometrical representation. The one or more boundaries may include an inflow boundary for the inflow boundary and an outflow boundary for each outflow boundary. The boundary condition for each outflow boundary may be determined using an outflow distribution parameter. The outflow distribution parameter may be determined using the geometry data for one or more of the one or more outflow boundaries, stored hemodynamic data, or a combination thereof. The processor may be configured to cause determining a flow field for each arterial segment using the geometrical representation, one or more of the boundary conditions, and pressure data, the flow field including pressure field. The processor may be further configured to cause determining hemodynamic information using the boundary conditions, the flow field, and pressure data for the patient.

In some embodiments, the processor may be further configured to cause display the generated geometrical representation and/or hemodynamic information on a user interface. In some embodiments, the processor may be configured to cause receiving information regarding a position of a virtual stent disposed along one or more segments of the geometrical representation displayed on the user interface; and generating an updated geometrical representation and/or hemodynamic information.

In some embodiments, the computer readable media may include a non-transitory computer readable medium storing instructions for determining a hemodynamic information for a patient. The instructions may include receiving medical image data of a patient acquired by a medical image acquisition device. The medical image data may include one or more arterial segments and surrounding area. The instructions may include generating a geometrical representation of the one or more arterial segments from the medical image data. The instructions may include determining boundaries and geometry data for each arterial segment. The boundaries may include an inflow boundary and one or more outflow boundaries. In some embodiments, the inflow boundary and the one or more outflow boundaries may correspond to a cross-section of each arterial segment. The geometry data may include a radius for the inflow boundary and a radius for each outflow boundary. The instructions may include determining one or more boundary conditions for the geometrical representation. The one or more boundary conditions may include an inflow boundary condition for the inflow boundary and an outflow boundary condition for each outflow boundary. The outflow boundary condition for each outflow boundary may be determined using an outflow distribution parameter. The outflow distribution parameter may be determined using the geometry data for one or more of the one or more outflow boundaries, stored hemodynamic data, or a combination thereof. The instructions may further include determining a flow field for each arterial segment using the geometrical representation, one or more of the boundary conditions, and pressure data; and determining hemodynamic information using one or more of the boundary conditions, the flow field, and pressure data for the patient.

In some embodiments, the instructions may further include displaying the generated geometrical representation and/or the hemodynamic information on a user interface. In some embodiments, the instructions may further include receiving information regarding a position of a virtual stent disposed along one or more segments of the geometrical representation displayed on the user interface; and generating an updated geometrical representation and/or hemodynamic information.

In some embodiments, the inflow boundary condition may be a stored value, determined from patient information, pools of patient data, among others, or a combination thereof.

In some embodiments, the one or more outflow boundaries may include a first outflow boundary and a second outflow boundary. The second outflow boundary may disposed between the first outflow boundary and the inflow boundary. In some embodiments, the one or more outflow boundaries may include a third outflow boundary. The third outflow boundary may be disposed between the first outflow boundary and the second outflow boundary.

In some embodiments, the one or more arterial segments may correspond to the one or more coronary arterial segments.

In some embodiments, the outflow distribution parameter may be determined using a ratio of a radius for the first outflow boundary and a radius for the second outflow boundary, and the stored hemodynamic data. In some embodiments, the stored hemodynamic data may define an empirical relationship between (i) the ratio of the radius of the first outflow boundary and the radius of the second outflow boundary and (ii) a ratio of an outflow boundary condition for the first outflow boundary and an outflow boundary condition for the second outflow boundary.

In some embodiments, the one or more outflow boundaries may include additional outflow boundaries disposed between the inflow boundary and the first outflow boundary. The outflow distribution parameter may be used to determine an outflow boundary condition for the first outflow boundary, the second outflow boundary, and each additional outflow boundary.

In some embodiments, the geometrical representation may correspond to a multi-dimensional digital model of a spatial volume of the one or more arterial segments. The geometrical representation of the one or more arterial segments may be discretized into a three-dimensional volumetric mesh. The geometrical representation may include a surface mesh representing a boundary of a vessel wall of each segment.

In some embodiments, the pressure field may be determined using only the geometrical representation, the geometrical data and one or more of the boundary conditions. In some embodiments, the flow field may include a velocity field.

In some embodiments, the medical image data may be magnetic resonance imaging (MRI), angiography, intravascular ultrasound (IVUS), optical coherence tomography (OCT), and/or computed tomography (CT) image data. In some embodiments, the image data may be computed tomography image data of one or more coronary arterial segments of a patient.

In some embodiments, the hemodynamic information may include fractional flow reserve (FFR), instantaneous wave-free ratio (iFR), wall shear stress (WSS), axial plaque stress (APS), hyperemic and resting diastolic pressure (Pd)/aortic pressure (Pa) indexes, pressure indices over a range of physiologic states, or a combination thereof.

In some embodiments, the methods may include a computer-implemented method of determining boundary conditions for a geometrical representation of an arterial anatomy of a patient. The method may include receiving medical image data of a patient acquired by a medical image acquisition device. The medical image data may include one or more arterial segments and surrounding area. The method may further include generating a geometrical representation of the one or more arterial segments from the medical image data. The method may further include determining boundaries and geometry data for each arterial segment. The boundaries may include an inflow boundary and one or more outflow boundaries. The inflow boundary and the one or more outflow boundaries may correspond to a cross-section of each arterial segment. The one or more outflow boundaries may include a first outflow boundary and a second outflow boundary. The second outflow boundary may be disposed between the first outflow boundary and the inflow boundary. The geometry data may include a radius for the inflow boundary and for each outflow boundary. The method may further include determining an outflow distribution parameter using the geometry data for one or more of the one or more outflow boundaries and stored hemodynamic data. The hemodynamic data may define an empirical relationship between (i) the ratio of the radius of the first outflow boundary and the radius of the second outflow boundary and (ii) a ratio of the outflow boundary condition for the first outflow boundary and the outflow boundary condition for second outflow boundary. The method may further include determining an outflow boundary condition for each outflow boundary using the outflow distribution parameter and the inflow boundary.

In some embodiments, the method may further include determining a flow field for each arterial segment using the geometrical representation, one or more of the boundary conditions, and pressure data, the flow field including a pressure field. The method may further include determining hemodynamic information using one or more of the boundary conditions, the flow field, and pressure data for the patient. In some embodiments, the flow field may include a velocity field.

In some embodiments, the systems may include a system determining boundary conditions for a geometrical representation of an arterial anatomy of a patient. The system may include at least one processor and a memory. The processor may be configured to cause receiving medical image data of a patient acquired by a medical image acquisition device. The medical image data may include one or more arterial segments and surrounding area. The method may further include generating a geometrical representation of the one or more arterial segments from the medical image data. The processor may be configured to cause determining boundaries and geometry data for each arterial segment. The boundaries may include an inflow boundary and one or more outflow boundaries. The inflow boundary and the one or more outflow boundaries may correspond to a cross-section of each arterial segment. The one or more outflow boundaries may include a first outflow boundary and a second outflow boundary. The second outflow boundary may be disposed between the first outflow boundary and the inflow boundary. The geometry data may include a radius for the inflow boundary and for each outflow boundary. The processor may be further configured to cause determining an outflow distribution parameter using the geometry data for one or more of the one or more outflow boundaries and stored hemodynamic data. The hemodynamic data may define an empirical relationship between (i) the ratio of the radius of the first outflow boundary and the radius of the second outflow boundary and (ii) a ratio of the outflow boundary condition for the first outflow boundary and the outflow boundary condition for second outflow boundary. The processor may be further configured to cause determining an outflow boundary condition for each outflow boundary using the outflow distribution parameter and the inflow boundary.

In some embodiments, the processor may be further configured to cause determining a flow field for each arterial segment using the geometrical representation, one or more of the boundary conditions, and pressure data. In some embodiments, the flow field may include a pressure field. The processor may be further configured to cause determining hemodynamic information using one or more of the boundary conditions, the flow field, and pressure data for the patient. In some embodiments, the flow field may include a velocity field.

In some embodiments, the computer readable media may include a non-transitory computer readable medium storing instructions for determining boundary conditions for a geometrical representation of an arterial anatomy of a patient. The instructions may include receiving medical image data of a patient acquired by a medical image acquisition device. The medical image data may include one or more arterial segments and surrounding area. The method may further include generating a geometrical representation of the one or more arterial segments from the medical image data. The instructions may further include determining boundaries and geometry data for each arterial segment. The boundaries may include an inflow boundary and one or more outflow boundaries. The inflow boundary and the one or more outflow boundaries may correspond to a cross-section of each arterial segment. The one or more outflow boundaries may include a first outflow boundary and a second outflow boundary. The second outflow boundary may be disposed between the first outflow boundary and the inflow boundary. The geometry data may include a radius for the inflow boundary and for each outflow boundary. The instructions may further include determining an outflow distribution parameter using the geometry data for one or more of the one or more outflow boundaries and stored hemodynamic data. The hemodynamic data may define an empirical relationship between (i) the ratio of the radius of the first outflow boundary and the radius of the second outflow boundary and (ii) a ratio of the outflow boundary condition for the first outflow boundary and the outflow boundary condition for second outflow boundary. The instructions may further include determining an outflow boundary condition for each outflow boundary using the outflow distribution parameter and the inflow boundary.

In some embodiments, the instructions may further include determining a flow field for each arterial segment using the geometrical representation, one or more of the boundary conditions, and pressure data, the flow field including a pressure field. The instructions may further include determining hemodynamic information using one or more of the boundary conditions, the flow field, and pressure data for the patient. In some embodiments, the flow field may include a velocity field.

In some embodiments, the one or more arterial segments may correspond to the one or more coronary arterial segments. The outflow distribution parameter may be determined using a ratio of a radius for the first outflow boundary and the second outflow boundary and the stored hemodynamic data. In some embodiments, the one or more outflow boundaries may include additional outflow boundaries disposed between the inflow boundary and the first outflow boundary.

In some embodiments, the hemodynamic information may include fractional flow reserve (FFR), instantaneous wave-free ratio (iFR), wall shear stress (WSS), axial plaque stress (APS), hyperemic and resting diastolic pressure (Pd)/aortic pressure (Pa) indexes, pressure indices over a range of physiologic states, or a combination thereof.

In some embodiments, the geometrical representation may correspond to a multi-dimensional digital model of a spatial volume of the one or more arterial segments. The geometrical representation of the one or more arterial segments may be discretized into a three-dimensional volumetric mesh. The geometrical representation may include a surface mesh representing a boundary of a vessel wall of each segment.

In some embodiments, the pressure field may be determined using only the geometrical representation, the geometrical data and the boundary conditions.

In some embodiments, the medical image data may be magnetic resonance imaging (MRI), angiography, intravascular ultrasound (IVUS), optical coherence tomography (OCT), and/or computed tomography (CT) image data. In some embodiments, the image data may be computed tomography image data of one or more coronary arterial segments of a patient.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

FIGS. 4A-E show examples of images to generate a geometrical representation according to embodiments;

DESCRIPTION OF THE EMBODIMENTS

Figure 1:
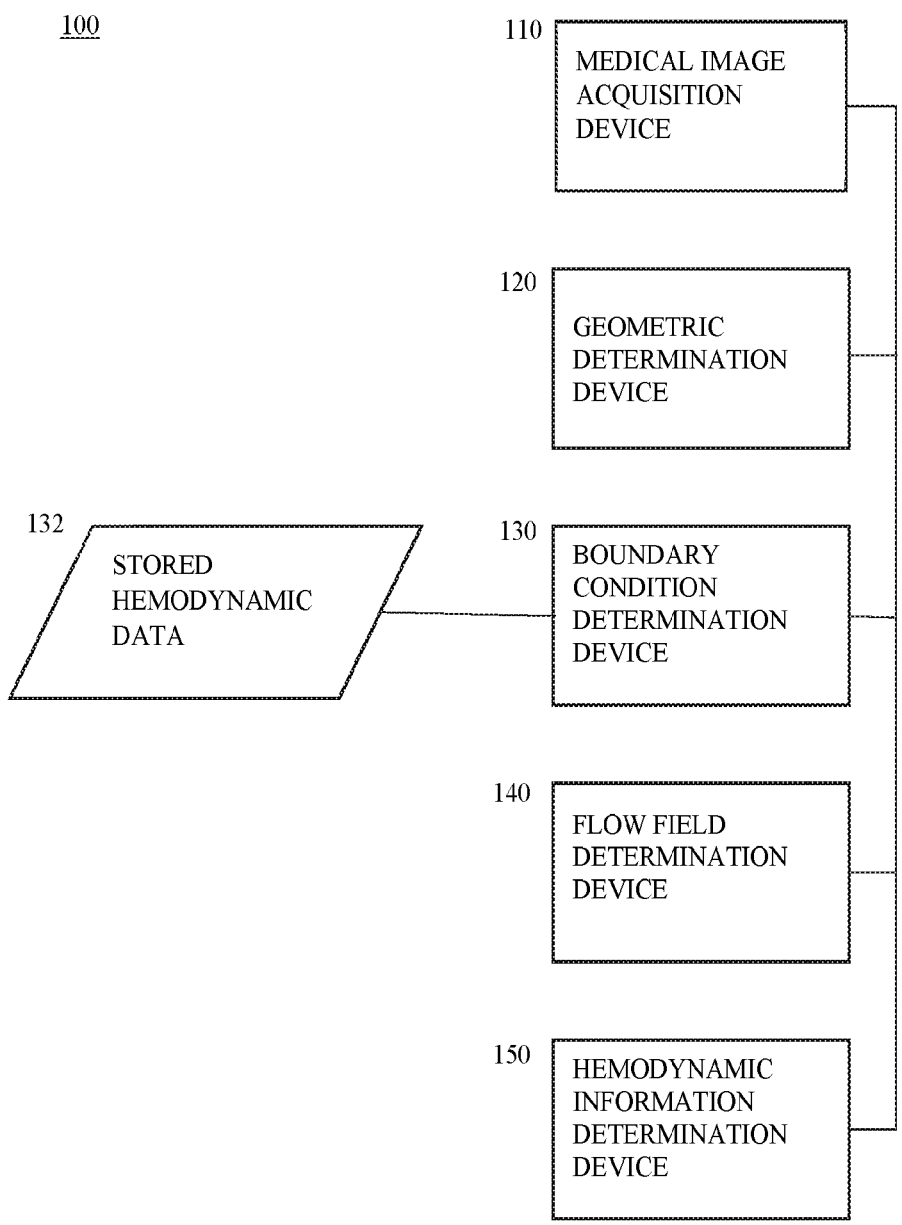
FIG. 1 shows an example of a system that can be used to determine hemodynamic information according to some embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The systems and methods of the disclosure can accurately determine boundary conditions for an arterial segment, such as a coronary arterial segment, and thereby determine hemodynamic information (e.g., fractional flow reserve (FFR), instantaneous wave-free ratio (iFR), wall shear stress (WSS), axial plaque stress (APS), hyperemic and resting diastolic pressure (Pd)/aortic pressure (Pa) indexes, pressure indices over a range of physiologic states, or a combination thereof) for that segment without requiring invasive measurements, such as flow measurements. Resting diastolic Pd/Pa have been shown to be similar to iFR. In contrast, hyperemic diastolic Pd/Pa may be more sensitive than FFR, in embodiments, as average diastolic flow is greater than the average flow over the whole cardiac cycle in coronary arteries. Additionally, recent results show that WSS may be predictive of myocardial infarction. APS as well may improve diagnostic and prognostic assessments relative to iFR and FFR. Furthermore, the systems and methods of the disclosure can efficiently and timely determine these measures without requiring significant computational requirements, such as super computer. Thus, the systems and methods can provide accurate boundary conditions and hemodynamic information, such as fractional flow reserve determinations, in a fairly rapid manner in a clinical setting at a minimal cost. This can provide a near real-time (e.g., relatively short-time) evaluation of a patient, for example, when a patient presents chest pain in a hospital emergency department, enabling a practitioner to make clinical decisions, thereby improving the quality of healthcare for a patient.

FIG. 1 shows a system 100 that can determine hemodynamic information for each geometrical representation of one or more arterial segments for a patient according to embodiments. In some embodiments, the system 100 may include a medical image acquisition device 110, a geometric determination unit 120, a boundary condition generation device 130, a flow field determination device 140, and a hemodynamic information determination device 150.

The medical image acquisition device 110 may be configured to acquire one or more medical images of a vascular system of a subject. In some embodiments, the medical image acquisition device 100 may include but is not limited to a computed tomography (CT) acquisition device, intravascular ultrasound (IVUS), biplane angiography, intravascular ultrasound (IVUS), optical coherence tomography (OCT), magnetic resonance imaging (MRI), among others, or a combination thereof. In some embodiments, the system 100 may include a medical image storage device configured to store the medical images acquired by the medical image acquisition device 100.

In some embodiments, the geometric representation determination unit 110 may be configured to generate a geometrical representation of one or more arterial segments from at least the acquired medical image data. The one or more arterial segments may include a portion of one or more arteries and one or more branches that extend therefrom.

In some embodiments, the one or more arterial segments may include one or more coronary arterial segments. The one or more coronary arterial segments may include a portion of one or more coronary arteries emanating from an aorta of a subject and one or more branches that extend therefrom. The one or more coronary arterial segments may include but is not limited to one or more portions of the left coronary artery (LCA) and/or the right coronary artery (RCA). The one or more coronary arterial segments for the left coronary artery (LCA) may include but is not limited to the left main coronary artery (LM), the left anterior descending (LAD), the left circumflex artery (also referred to as the "Circumflex"), among others, or a combination thereof.

The disclosure is discussed in reference to coronary arterial segments. However, it will be understood that the one or more arterial segments are not limited to the coronary arterial segments discussed and may include other coronary arterial segments, other types of arterial segments, among others, or a combination thereof. For example, the one or more arterial segments may include cerebral arterial segment(s), femoral arterial segment(s), iliac arterial segment(s), popliteal arterial segment(s), carotid arterial segment(s), and the like.

In some embodiments, the geometrical representation may be a multi-dimensional (3-D) digital model of the spatial volume of one or more arterial segments. For example, the geometrical representation of one or more arterial segments may be discretized into a three-dimensional volumetric mesh, for example, polyhedrons (e.g., tetrahedrons). In some embodiments, the geometrical representation may include a surface mesh representing the boundary of the lumens of each arterial segment.

In some embodiments, the geometric representation determination unit 110 may be configured to determine boundaries for each arterial segment. "Boundaries" may refer to cross-sections of the representation of the arterial segment and may include but are not limited to: inflow boundary corresponding to the cross-section through which the blood flows; one or more outflow boundaries corresponding to the cross-section disposed downstream or distal from the inflow boundary through which blood flow is directed outward; one or more vessel wall boundaries corresponding to an interface between the inner surface of the arterial wall and the flowing blood; among others; or combination thereof.

In some embodiments, the one or more outflow boundaries may include an outflow boundary disposed at or adjacent to a junction point (e.g., bifurcation, trifurcation, and the like, and combinations thereof). In some embodiments, the one or more outflow boundaries may include an outflow boundary disposed at or adjacent to the left Circumflex artery. In some embodiments, the one or more outflow boundaries may include a first outflow boundary and a second outflow boundary that is disposed between the inflow boundary and the first outflow boundary. In some embodiments, the first outflow boundary may correspond to a distal boundary of the segment (i.e., the cross-section disposed downstream or distal from the inflow boundary). In some embodiments, for example, when the geometrical representation includes the left coronary artery, the second outflow boundary may correspond to the circumflex. In some embodiments, the first outflow boundary and the second outflow boundary may be separated by one or more additional outflow boundaries, for example, at least a third outflow boundary. The third outflow boundary may correspond to or be adjacent to a junction point, such as a branch or bifurcation.

In some embodiments, the geometric representation determination unit 110 may be configured to determine geometrical data for each boundary using the generated geometric representation. In some embodiments, the geometrical data may include but is not limited to radius, diameter, circumference, area, among others, or a combination thereof.

In some embodiments, the boundary condition determination device 130 may be configured to determine boundary conditions for each boundary for each arterial segment. By way of example, the boundary conditions for each segment may include inflow boundary condition, outflow boundary conditions, one or more vessel wall boundary conditions, among others, or a combination thereof. The inflow boundary condition may be a value or a range of values for velocity, flow rate, pressure or other characteristic. Each outflow boundary condition may be a value or a range of values for velocity, flow rate, pressure, a percentage of inflow boundary, or other characteristic. Each vessel wall boundary condition may be a value or a range of values for velocity, flow rate, pressure, a combination thereof, or other characteristic.

In some embodiments, the determination of the inflow boundary condition and/or outflow boundary conditions may be determined based on patient information, resting state, hyperemic state, other physiologic states (e.g., walking, various levels of exercise, etc.), the type of segment (e.g., LCA or RCA), among others, or a combination thereof.

In some embodiments, the inflow boundary condition may be a stored value and/or specified by the user.

In some embodiments, the outflow boundary conditions may be determined using an outflow distribution parameter. The outflow distribution parameter may be determined using the geometrical data and/or stored hemodynamic data 132. The hemodynamic data 132 may define or be used to define an empirical relationship between radii of outflow boundaries and respective flow rates. For example, the boundary condition generation device 130 can determine the outflow distribution parameter using the stored hemodynamic data 132 and the radii of the first and second outflow boundaries of the segment. In another example, the boundary condition generation device 130 can determine the outflow distribution parameter using only geometrical data, for example, the radius of the first outflow boundary (the distal boundary) of the segment. The outflow distribution parameter can be used to determine outflow (e.g., velocity, flow rate, percentage of inflow) for each outflow boundary, thereby determining each outflow boundary condition.

By way of example, the boundary conditions determined by the boundary condition determination device 130 can be used with steady and/or unsteady flow computations to determine flow field (e.g., blood flow, pressure field, velocity field, wall shear stress, etc.) and other hemodynamic information (e.g., FFR, iFR, etc.). The boundary condition determination device 130 also uses an optimization approach to define the artery segment flow splitting. Therefore, the boundary condition generation device 130 can provide flexibility, accuracy, and efficiency in determining the boundary conditions.

In some embodiments, the flow field determination device 140 may be configured to determine a flow field for each arterial segment using the geometrical representation, the one or more boundary conditions and the pressure data for the patient. In some embodiments, the flow field may include but is not limited to pressure field, velocity field, wall shear stress field, axial plaque stress, among others, or a combination thereof.

In some embodiments, a flow field parameter (e.g., pressure field, velocity, etc.) may be based on only the geometrical data and boundary conditions. This way, the flow field determination device 140 may be configured to determine the flow field based only spatial location (i.e., independent of time).

In some embodiments, the hemodynamic information determination device 150 can be configured to determine hemodynamic information for the patient using the boundary conditions determined by the boundary condition generation device 130, the flow field determined by the flow field determination device 140, and patient specific pressure data. In some embodiments, the pressure data can be determined from a computed flow/pressure field, a non-invasive determination of a mean blood pressure of the patient, for example, determined by a blood pressure cuff, among others, or a combination thereof. The hemodynamic information may include but is not limited to fractional flow reserve (FFR), coronary flow reserve (CFR), instantaneous wave-free ratio (iFR), hyperemic stress reserve (HSR), basal stenosis resistance (BSR), microcirculatory resistance (IMR), wall shear stress (WSS), axial plaque stress (APS), hyperemic and resting diastolic pressure (Pd)/aortic pressure (Pa) indexes, pressure indices over a range of physiologic states, among others, or a combination thereof. By way of example, for the FFR, iFR, pressure ratios, and pressure indices, the hemodynamic information may include but is not limited to: continuous pressure ratio for the segment; a discrete pressure value corresponding to a location on the geometrical representation displayed on the user interface selected by the user on the interface; among others; or combination thereof.

In some embodiments, the hemodynamic information can be used to determine functional assessment of one or more stenoses. In some embodiments, the hemodynamic information determination device can generate virtual intervention simulations using the hemodynamic information and geometric representation for decision support and intervention planning.

The hemodynamic information determination device 150 may interface with a user interface on which the geometrical representation may be displayed so that the user may select the location on the geometrical representation at which the hemodynamic information (e.g., computed pressure ratio) is determined; modify the geometrical representation for example, by removing the localized stenosis so that the hemodynamic information can be updated; among others; or a combination thereof. This way, clinicians can be capable of making near real-time decisions when evaluating patients.

In some embodiments, the medical image acquisition device 110, the geometric determination device 120, the boundary condition generation device 130, the flow field determination device 140, and the hemodynamic information determination device 150, as well as the stored hemodynamic data 132, may have connectivity via a communication network. By way of example, the communication network of system 100 can include one or more networks such as a data network, a wireless network, a telephony network, or any combination thereof. The data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, NFC/RFID, RF memory tags, touch-distance radios, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WiFi), wireless LAN (WLAN), Bluetooth®, Internet Protocol (IP) data casting, satellite, mobile ad-hoc network (MANET), and the like, or any combination thereof.

Although the systems/devices of the system 100 are shown as being directly connected, the systems/devices may be indirectly connected to one or more of the other systems/devices of the system 100. In some embodiments, a system/device may be only directly connected to one or more of the other systems/devices of the system 100.

It is also to be understood that the system 100 may omit any of the devices illustrated and/or may include additional systems and/or devices not shown. It is also to be understood that more than one device and/or system may be part of the system 100 although one of each device and/or system is illustrated in the system 100. It is further to be understood that each of the plurality of devices and/or systems may be different or may be the same. For example, one or more of the devices of the devices may be hosted at any of the other devices. By way of another example, the boundary condition determination device 130 may communicate with a different hemodynamic information determination device.

Figure 6:
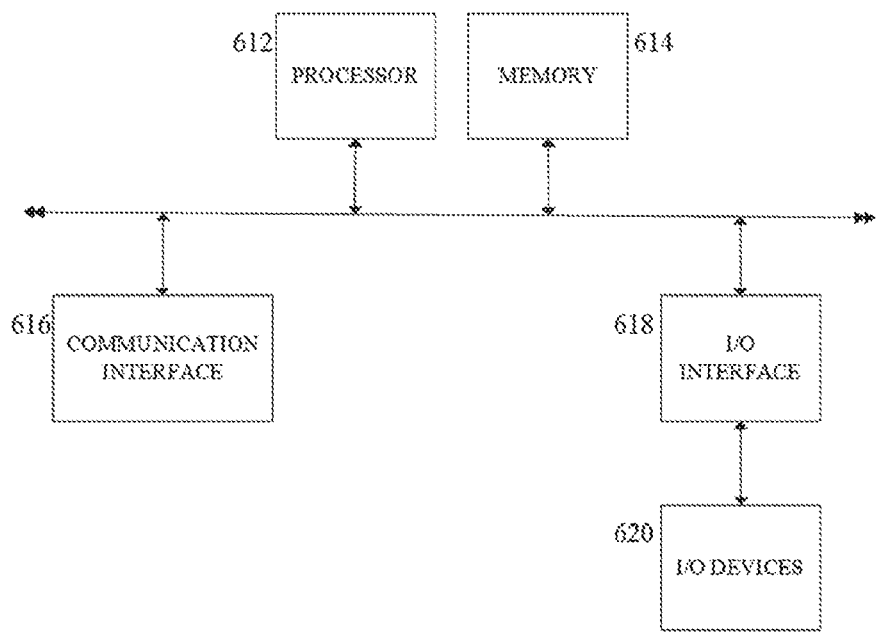
FIG. 6 shows a block diagram illustrating an example of a computing system.

In some embodiments, any of the devices of the system 100 may include a non-transitory computer-readable medium storing program instructions thereon that is operable on a user device. A user device may be any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, or any combination thereof, including the accessories and peripherals of these devices, or any combination thereof. FIG. 6 shows an example of a user device.

FIGS. 2-5 show methods of determining hemodynamic information for a geometrical representation for one or more arterial segments according to embodiments. Unless stated otherwise as apparent from the following discussion, it will be appreciated that terms such as "updating," "modifying," "generating," "determining," "displaying," "obtaining," "processing," "computing," "selecting," "receiving," "detecting," "estimating," "calculating," "quantifying," "outputting," "acquiring," "analyzing," "retrieving," "inputting," "assessing," "performing," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. The system for carrying out the embodiments of the methods disclosed herein is not limited to the systems shown in FIGS. 1 and 6. Other systems may also be used.

The methods of the disclosure are not limited to the steps described herein. The steps may be individually modified or omitted, as well as additional steps may be added. It will be also understood that at least some of the steps may be performed in parallel.

Figure 2:
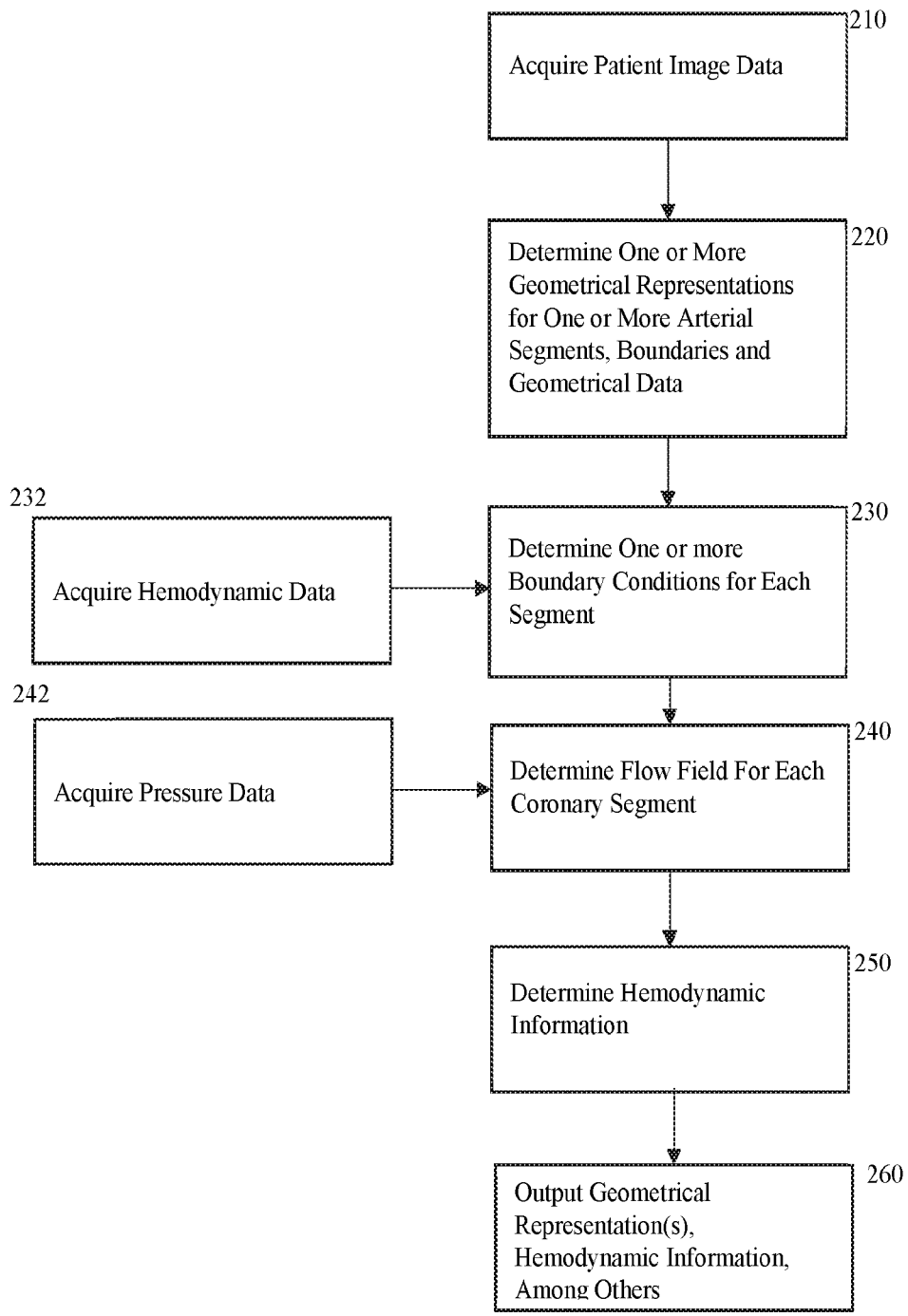
FIG. 2 shows a method of determining hemodynamic information according to some embodiments.

FIG. 2 illustrates a method 200 for determining hemodynamic information for one or more arterial segments for a patient according to some embodiments.

In some embodiments, the method 200 may include a step 210 of receiving medical image data of a patient acquired by a medical imaging system, such as the medical imaging system 110. The image data may include but is not limited to CT image data, biplane angiography, intravascular ultrasound (IVUS), optical coherence tomography (OCT), magnetic resonance imaging (MRI), among others, or a combination thereof. The image data may include one or more regions of surrounding blood vessels, including the arteries, of a patient.

By way of example, the medical image data may be digitized image data obtained from cardiac CT scans of a patient using a clinical CT system. In some embodiments, the image data may include one or more image slices of a region of interest which may include the arteries of interest and surrounding blood vessel. In addition to CT images, the image data may be from other sources, such as biplane angiography, intravascular ultrasound (IVUS), optical coherence tomography (OCT), magnetic resonance imaging (MRI), among others, or combination thereof.

In some embodiments, the image data of the patient may be presented to the user to select the one or more arterial segments for which the hemodynamic information should be generated. In the alternative, the system may automatically determine which arterial segments should the hemodynamic information be analyzed.

Next, in some embodiments, the method 200 may include a step 220 of determining a geometrical representation for one or more arterial segments from the CT image data of the patient. In some embodiments, the geometrical representation may be a multi-dimensional (3-D) digital model of the spatial volume of one or more arterial segments. The geometrical representation of one or more arterial segments may be discretized into a three-dimensional mesh volumetric mesh, for example, polyhedrons (e.g., tetrahedrons). In some embodiments, the geometrical representation may include a surface mesh representing the boundary of the vessel wall (e.g., lumens) of each arterial segment.

The step 220 may include determining boundaries for each arterial segment using the geometrical representation and determining geometrical data associated with each boundary for each segment. For each segment, the boundaries may include inflow boundary, one or more outflow boundaries, vessel wall boundaries, among others, or a combination thereof. For example, in this step, the geometrical data may include determining the radii for the inflow boundary and for one or more outflow boundaries.

Next, the method 200 may include a step 230 of determining one or more boundary conditions for each segment of the geometrical representation. The one or more boundary conditions may include inflow boundary conditions, one or more outflow boundary conditions, and one or more vessel wall boundary conditions.

In some embodiments, the step 230 may include determining the inflow boundary condition. The inflow boundary condition may be a stored value, inputted by the user, determined from obtained patient information (e.g., cardiac output, myocardial mass, etc.), among others, or a combination thereof. In some embodiments, the system may store one or more values for the inflow boundary condition and selection may be based on hemodynamic information analysis to be performed, type of medical imaging data (e.g., CT data with nitroglycerine, CT data without nitroglycerine, etc.), among others, or a combination thereof. For example, the system may store one or more different values for the inflow boundary condition for FFR analysis (e.g., hyperemic state or high flow) and for the iFR analysis (e.g., baseline or normal flow), or for diastolic pressure (Pd)/aortic pressure (Pa) analysis over a range of physiologic states.

In some embodiments, the step 230 may include determining one or more outflow boundary conditions using the outflow distribution parameter. The outflow distribution parameter can be determined using the geometric data and/or the stored hemodynamic data.

In some embodiments, if the outflow distribution parameter is determined using the stored hemodynamic data and geometric data, the method 200 may include a step 232 of acquiring hemodynamic data stored locally on the system or remotely to determine the outflow distribution parameter. The outflow distribution parameter may be determined using a ratio of outflow boundaries determined from a ratio of associated outflow boundary point radii using the hemodynamic data.

In some embodiments, if the outflow distribution parameter is determined only using the geometric data, the outflow distribution parameter may be determined using the radii of an outflow boundary.

In some embodiments, the step 230 may include determining one or more vessel wall boundary conditions. In some embodiments, the one or more vessel wall boundary conditions may be determined using a null boundary condition (i.e., zero velocity) on the vessel wall, a positive boundary condition, among others, or a combination thereof.

Next, the method may include a step 240 of determining the flow field for each arterial segment using the geometrical representation (step 210), the one or more boundary conditions and the pressure data (e.g., aortic pressure data). In some embodiments, the pressure data may be obtained for the patient, for example, cuff pressure, and/or may be a stored value. In some embodiments, the flow field may include but is not limited to pressure field, velocity field, among others, or a combination thereof.

In some embodiments, the velocity field and/or pressure field may be determined based only on the boundaries and the boundary conditions. For example, the velocity field and/or pressure field may be determined using a steady flow Navier-Stokes equation in which the velocity and pressure variables are functions of only spatial location (i.e., time is not considered). This way, pressure and velocity can be accurately and efficiently be determined in in near real-time so as to enable point of care analysis by the clinician.

In some embodiments, the method 200 may include a step 242 of acquiring the pressure data. In some embodiments, the pressure data may correspond to hyperemia. In some embodiments, the pressure data may correspond to pressure of the patient acquired noninvasively. For example, the pressure data may be determined from the mean pressure data measured by brachial cuff.

Next, the method 200 may include a step 250 of determining hemodynamic information using the pressure data from step 242 and the flow field (e.g., pressure and/or velocity fields) determined in step 240. In some embodiments, the hemodynamic information may include but is not limited to fractional flow reserve (FFR), coronary flow reserve (CFR), instantaneous wave-free ratio (iFR), hyperemic stress reserve (HSR), basal stenosis resistance (BSR), microcirculatory resistance (IMR), wall shear stress (WSS), axial plaque stress (APS), hyperemic and resting diastolic pressure (Pd)/aortic pressure (Pa) indexes, pressure indices over a range of physiologic states, among others, or a combination thereof.

By way of example, for the FFR and iFR determinations, the continuous pressure ratio for the segment and/or a discrete pressure value corresponding to a location on the geometrical representation displayed on the user interface selected by the user on the interface may be determined. For the FFR determination, the pressure ratio and/or discrete pressure value may be for high or hyperemic flow (e.g., characterized by a value for inflow boundary condition) and may be determined using the pressure data and the pressure field determined in step 240. For the iFR determination, the pressure ratio and/or discrete pressure value may be for normal or baseline flow (e.g., characterized by a value for inflow boundary condition) and may be determined using the pressure data and the pressure field determined in step 240. For the determination of hyperemic and resting diastolic pressure (Pd)/aortic pressure (Pa) indexes, the pressure ratio and/or discrete pressure value may be calculated for diastolic flow (e.g., characterized by a value for inflow boundary condition over the diastolic period of the cardiac cycle, or over a subset of the diastolic period of the cardiac cycle) for high or hyperemic and normal or baseline flow, respectively. For determination of pressure indices over a range of physiologic states, a pressure index (e.g., a pressure ratio, a difference of pressure at two different geometric location, a ratio of a difference of pressure at two different geometric location and a normalizing pressure value, such as cuff pressure or aortic pressure), the pressure ratio and/or discrete pressure value may be calculated for a range of flow values characterizing different physiological states, such as hyperemic and resting or normal states, and other physiologic states representing a range of physical activities, such as walking, mild exercise, vigorous exercise, etc., the flow value being over the entire cardiac cycle or over the diastolic period only, or over any subset of the diastolic period.

In some embodiments, the WSS may be determined using the velocity field. In some embodiments, the APS may be determined using both the pressure and velocity fields. WSS and APS can be averaged over regions of the boundary wall, such as over a plaque or a lesion or any region of interest, to provide localized information. The determination of a plaque or a lesion or any region of interest of the boundary wall may be determined using the boundary wall geometric characteristics, the pressure and velocity fields, or a combination thereof. The WSS and APS can be determined in addition to the iFR determination, the FFR determination, determination of hyperemic and resting diastolic pressure (Pd)/aortic pressure (Pa) indexes, determination of pressure indices over a range of physiologic states or a combination thereof.

Next, the method 200 may include a step of 260 of outputting the hemodynamic information, the geometrical representation(s), among others. For example, the values for the hemodynamic information may be displayed on a user interface (e.g., display device). In some embodiments, the values for the hemodynamic information can be displayed by overlaying those values at their corresponding locations on the associated geometrical representation on the user interface.

It will be understood that the user may modify the geometrical representation and/or the boundary conditions, for example, to model one or more treatments, e.g., placing a coronary stent (e.g., virtual stenting to thereby remove one or more stenosis) in one or more of the coronary arterial segments represented in the geometrical representation. Then, the computational analysis may be performed as described above in order to generate an updated geometrical representation and/or hemodynamic information, for example, to determine whether there is a change in blood flow velocity and/or pressure if the treatment option(s) is adopted. The one or more generated geometrical representations and/or hemodynamic information may be displayed to the user (e.g., clinician) on the user interface.

Generating A Geometrical Representation

Figure 3:
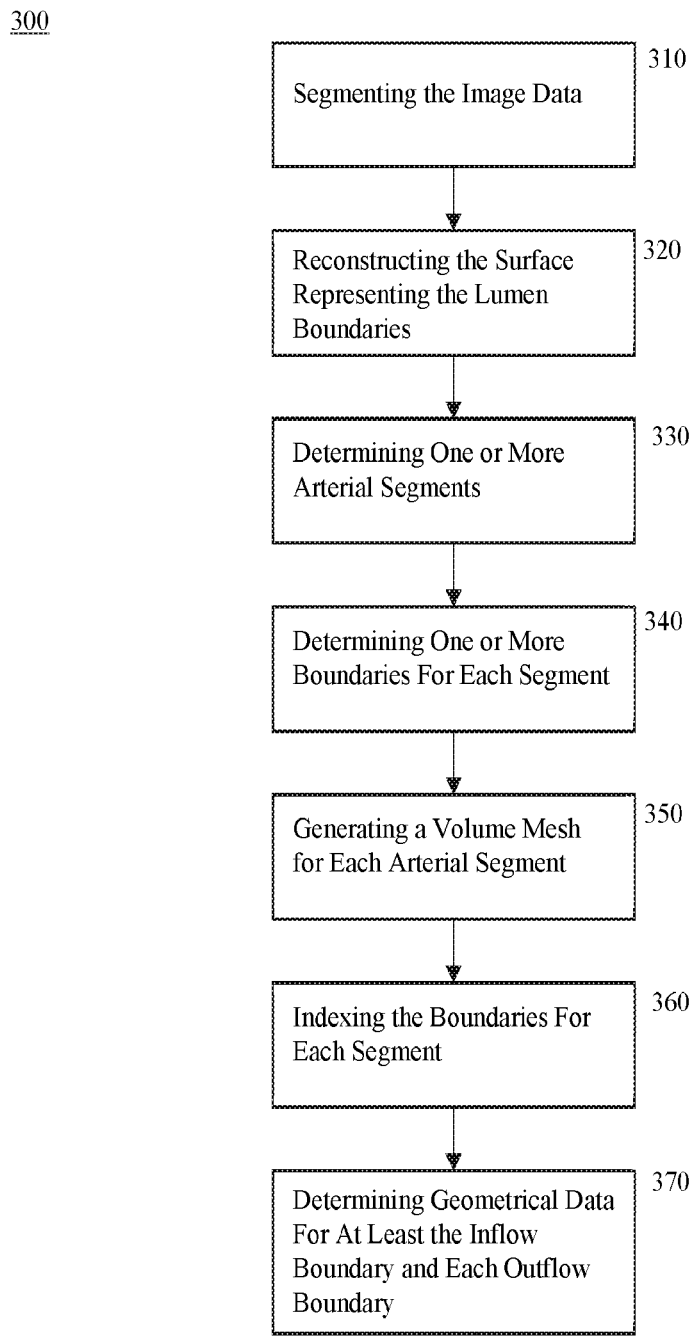
FIG. 3 shows a method of generating a geometrical representation of one or more arterial segments using medical image data according to some embodiments.

FIG. 3 shows a method 300 of generating a geometrical representation for one or more arterial segments and determining boundaries and geometrical data associated with the boundaries using the generated geometrical representation.

Figure 4A:
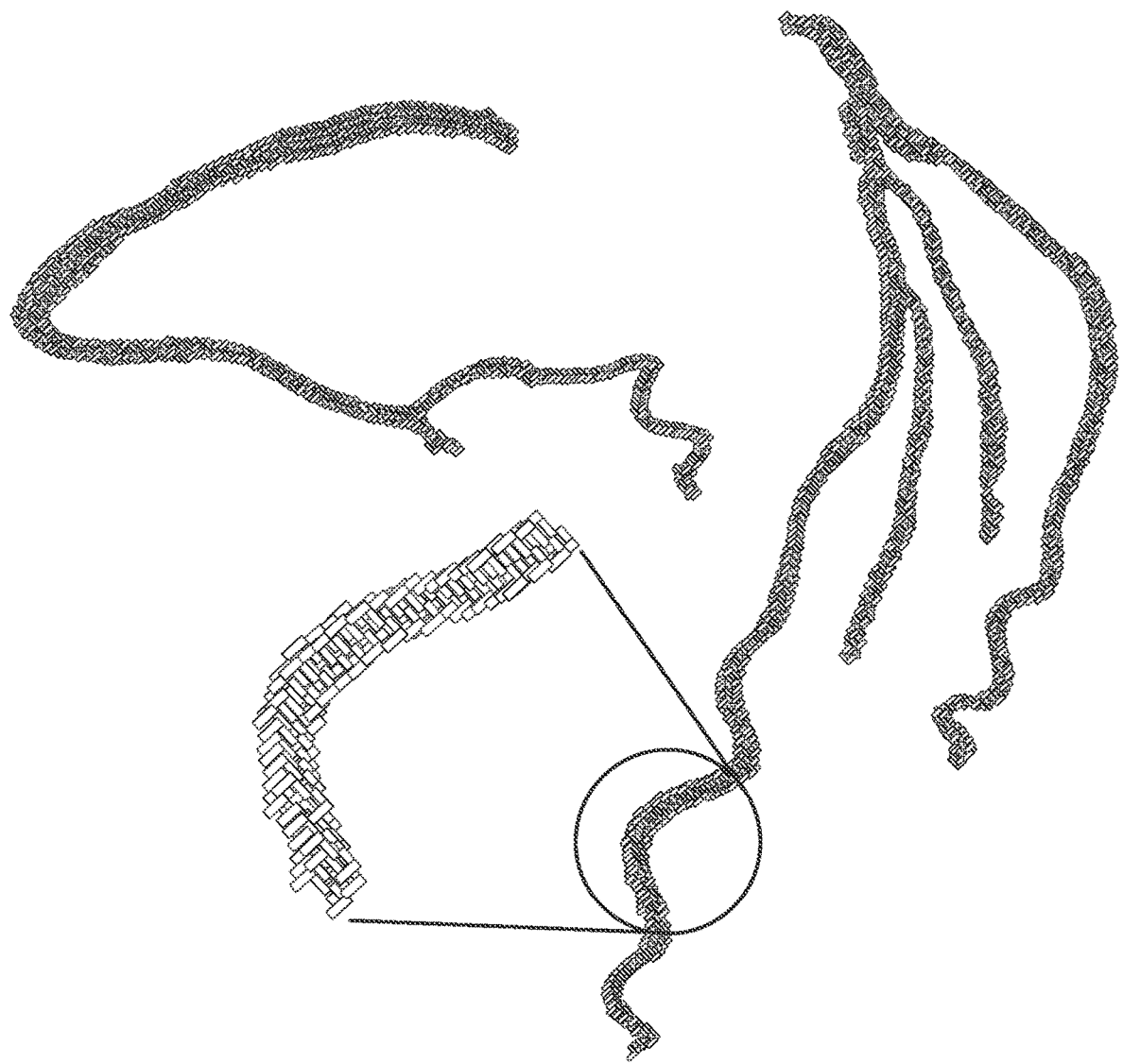

In some embodiments, the method 300 may include a step 310 of segmenting the image data to generate a 3D geometrical representation of one or more major blood vessels including the one or more coronary arterial segments. FIG. 4A shows an example of segmented CT image data.

Figure 4B:
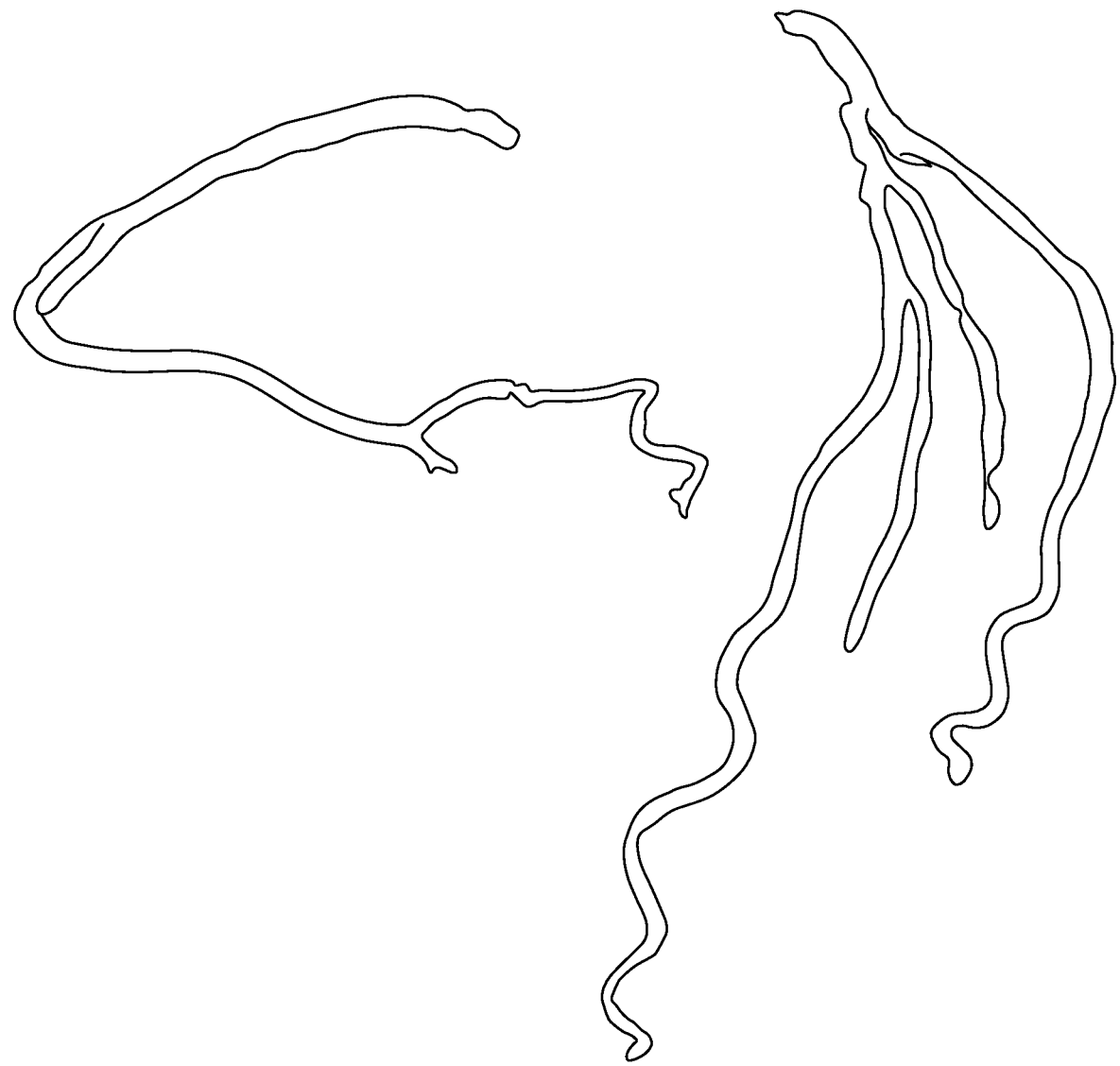

Next, the method 300 may include a step 320 of reconstructing the surface representing the vessel wall (e.g., lumen boundaries) of each arterial segment provided in the segmented image. In some embodiments, the step 320 may include generating a surface mesh for the area/interface between the vessel wall and the flowing blood, and further smoothing the surface mesh to reduce surface irregularities, for example due to local artifacts. For example, the surface mesh may be generated using marching cube, restricted delaunay triangulation, among others, or a combination thereof. FIG. 4B shows the reconstructed surface from the segmented image shown in FIG. 4A.

Next, the method 300 may include a step 330 of determining one or more arterial segments from processed image data (step 320). For example, with respect to the coronary arterial segments, the one or more arterial segments may include the RCA, the LCA, the left anterior descending geometry, the left main geometry, and/or a left circumflex (LCx).

In some embodiments, the step 330 may include decoupling the one or more arterial segments to be analyzed, such as RCA and LCA, from the surrounding vessels, such as aorta and other tree structures.

Figure 4C:
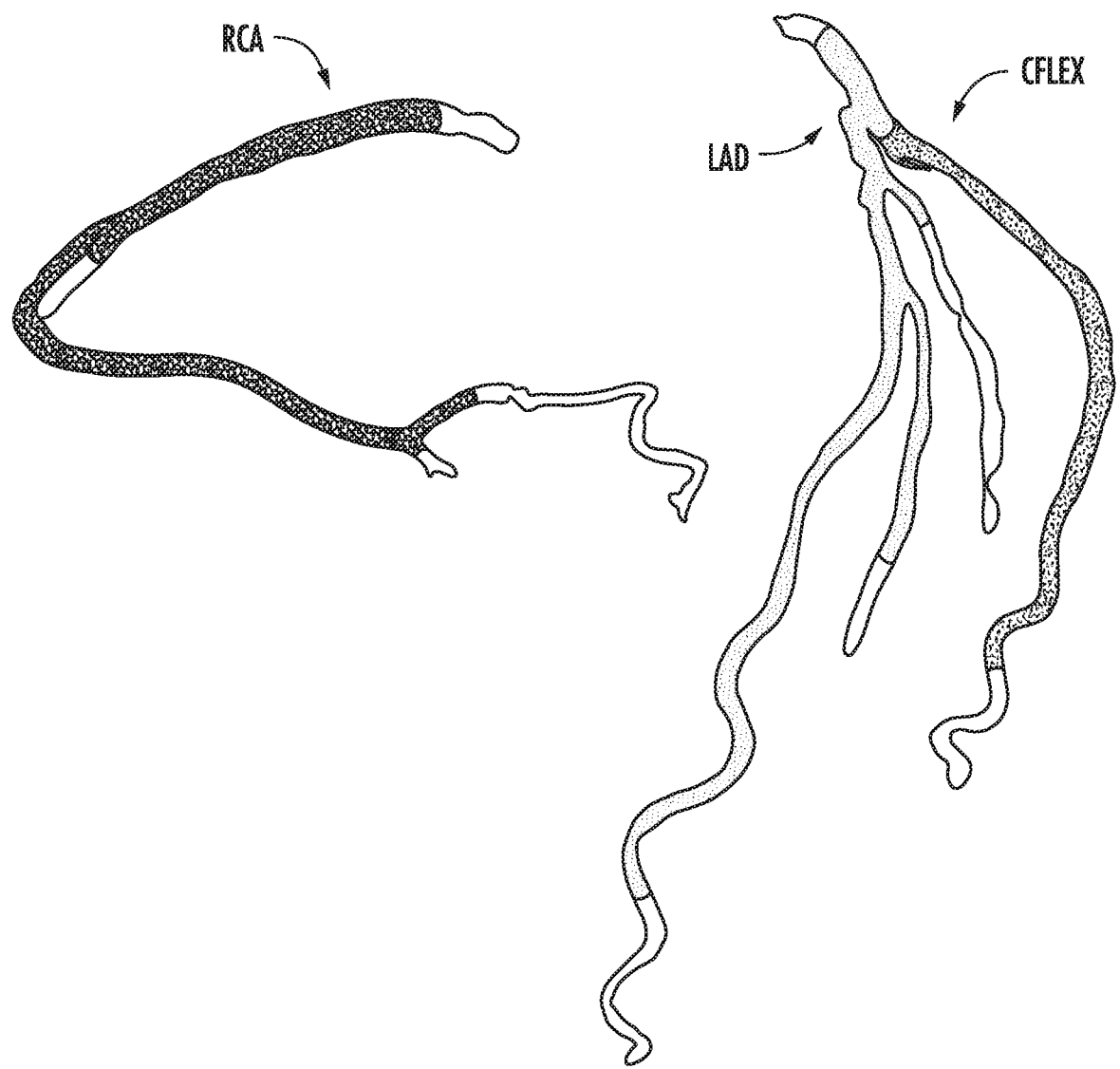

In some embodiments, the step 330 may further include clipping or trimming the decoupled segments into one or more arterial segments. For example, the LCA may be separated into two segments: 1) LM/LAD and 2) circumflex so one or both of these segments may be separately analyzed. FIG. 4C shows the segmented image shown in FIG. 4B labeled with the different segments.

In some embodiments, the method 300 may include a step 340 of determining and identifying the boundaries associated each segment. For example, the boundaries may include an inflow boundary (Bin), one or more outflow boundaries, vessel wall boundary, or a combination thereof. In some embodiments, the one or more outflow boundaries (e.g., Bi, Bd, Bc, Bi+1) may include a first outflow boundary and a second outflow boundary that is disposed between the inflow boundary and the first outflow boundary. In some embodiments, the first outflow boundary may correspond to the distal boundary of the segment (e.g., Bd). In some embodiments, for example, when the geometrical representation includes a left coronary artery, the second outflow boundary may correspond to the circumflex (Bc). In some embodiments, the first outflow boundary and the second outflow boundary may be separated by the third outflow boundary.

In some embodiments, the method 300 may include a step 350 of generating a volume mesh for each segment. The volume mesh, represented by a plurality of volume elements, may discretize the volume of the geometrical representation. For example, the system may include filling the interior of each geometry with the plurality of volume elements. The volume elements may take the form of any closed polyhedron, including but not limited to tetrahedra, hexahedra, wedges, among others, or a combination thereof.

In some embodiments, the method may include a step 360 of indexing the boundaries with respect to each segment. The boundaries for each segment may be indexed with a separate identifier, with a different color in the representation, among others, or a combination thereof. By way of example, each boundary may be shown with a different color in the geometrical representation. FIG. 4D shows an example of an isolated segment of a generated geometrical representation 440 (from step 350) with the inflow boundary 442 and an outflow boundary 444 identified and indexed.

In some embodiments, the method 300 may include a step 370 of determining geometrical data for the boundaries for each segment. In this example, the geometrical data may include determining the radius for the inflow boundary and each outflow boundary for each segment.

Figure 4E:
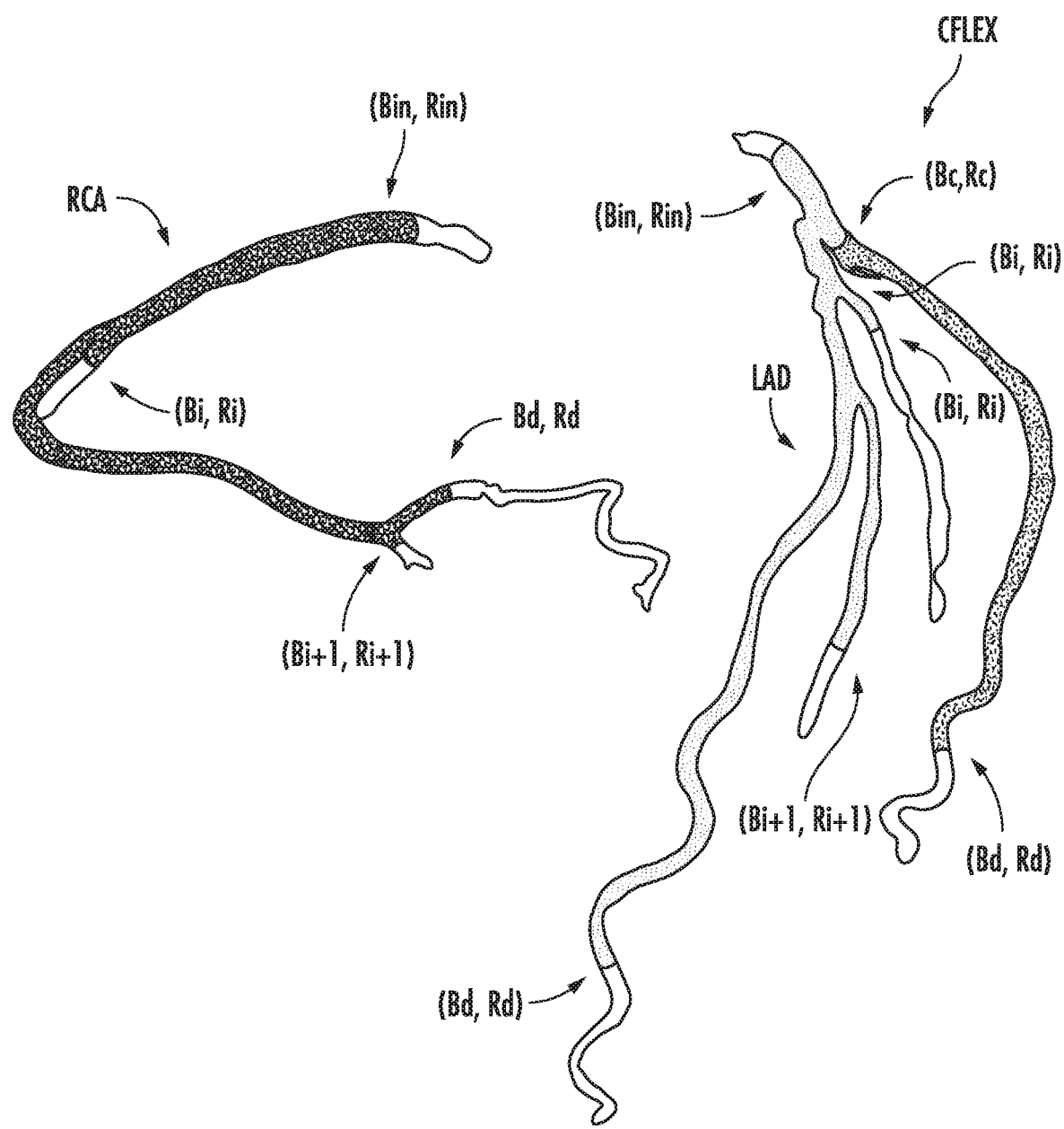

FIG. 4E shows an example of a labeled geometrical representation having the following coronary arterial segments: 1) LAD with a portion of the LM; 2) Circumflex; and 3) RCA. In this example, for each segment, the boundaries have been identified and the radii (R) have been determined for each boundary. As shown in this example, for the segment corresponding to the LAD and a portion of the LM, the boundaries and associated radii may include: inflow boundary (Bin) and associated radius (Rin); circumflex boundary (Bc) and associated radius (Rc); additional outflow boundary (Bi) and associated radius (Ri); and distal outflow boundary (Bd) and associated radius (Rd). For the segment corresponding to the left circumflex (Cflex), the boundaries and associated radii may include: inflow boundary (Bin) and associated radius (Rin); first additional outflow boundary (Bi) and associated radius (Ri); second additional outflow boundary (Bi+1) and associated radius (Ri+1); and distal outflow boundary (Bd) and associated radius (Rd). For the segment corresponding the left right coronary artery (RCA), the inflow boundary (Bin) and associated radius (Rin); additional outflow boundary (Bi) and associated radius (Ri); and distal outflow boundary (Bd) and associated radius (Rd).

Determining Boundary Conditions

Figure 5:
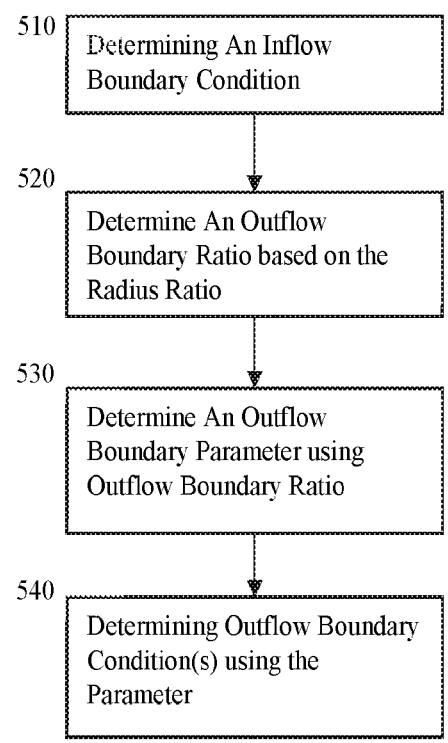
FIG. 5 shows a method of determining boundary conditions according to embodiments.

FIG. 5 shows a method 500 for determining boundary conditions for each boundary for each segment using the outflow distribution parameter according to some embodiments. In some embodiments, the outflow distribution parameter may be determined using the geometrical data for the segment and/or stored hemodynamic data.

In some embodiments, the method 500 may include the step 510 of determining the inflow boundary condition (Qin). The inflow boundary condition may be specified by the user; default value stored in the system, for example, based on the segment type; based on the patient information (e.g., BMI, cardiac mass, age, sex, whether the patient received nitroglycerin, etc.); based on the hemodynamic information analysis to be performed (e.g., iFR or FFR); based on a range of physiologic activity (e.g., rest, hyperemia, level of exercise, etc.) among others; or a combination thereof.

In some embodiments, the outflow distribution parameter may be determined using the geometrical data and the stored hemodynamic data.

In some embodiments, the method 500 may include a step 520 of determining an outflow boundary condition ratio based on the associated radii ratio (i.e. radii of the respective outflow boundaries of the segment). In some embodiments, the step 520 may include determining the outflow boundary condition ratio (i.e., ratio of flow rates) between one or more of the outflow boundaries using (i) the acquired hemodynamic data that define an empirical relationship between radii of outflow boundaries and respective flow rates and (ii) associated radii ratio of the segments. For example, the radii for the first outflow boundary and the second outflow boundary may be used to determine the outflow condition ratio.

By way of example, for the LM+LAD segment, a ratio $(R_c/R_d)$ for the radii for the distal outflow boundary $(R_d)$ and the circumflex boundary $(R_e)$ may be used to determine the outflow boundary ratio $(Q_c/Q_d)$ of outflow flow rates between these outflow boundaries using the stored hemodynamic data.

In some embodiments, the method 500 may include a step 530 of determining an outflow distribution parameter (k) based on the outflow boundary condition ratio determined from the stored hemodynamic data and radii for segments. By way of example for the segment including the LM+LAD, the outflow distribution parameter may correspond to the following adaptation of the well known Murray's law (a.k.a., cubic law):

$$k \approx \left( \frac{Q_c}{Q_d} \left( \frac{R_{in}}{R_c} \right)^3 \right)^{-1}.$$

The present system is not limited to the cubic law, and other power parameters different from exponent 3 may be considered, typically within the range of 2 and 3.

In some embodiments, the outflow distribution parameter may be determined using geometrical data only. In some embodiments, steps 520 and 530 may be modified and/or omitted. The outflow distribution parameter may be determined using only the radius for the outflow boundary. By way of example, the outflow distribution parameter may correspond to the following adaptation of the well-known Murray's law $k \approx Q_d/R_d^3$ (a.k.a., cubic law). The present system is not limited to the cubic law, and other power parameters different from exponent 3 may be considered, typically within the range of 2 and 3.

Next, the method 500 may include a step 540 of determining each outflow boundary condition including the distal outflow boundary condition using the outflow distribution parameter and the inflow boundary condition. For example, in some embodiments, the step 540 may include using least squares minimization approach to determine the flow rate distribution among the outflow boundaries of the segment.

Computer System

One or more of the devices and/or systems of the system 100 may be and/or include a computer system and/or device. FIG. 6 is a block diagram showing an example of a computer system 600. The modules of the computer system 600 may be included in at least some of the systems and/or modules, as well as other devices and/or systems of the system 100.

The system for carrying out the embodiments of the methods disclosed herein is not limited to the systems shown in FIGS. 1 and 6. Other systems may also be used. It is also to be understood that the system 600 may omit any of the modules illustrated and/or may include additional modules not shown.

The system 600 shown in FIG. 6 may include any number of modules that communicate with each other through electrical or data connections (not shown). In some embodiments, the modules may be connected via any network (e.g., wired network, wireless network, or a combination thereof).

The system 600 may be a computing system, such as a workstation, computer, or the like. The system 600 may include one or more processors 612. The processor(s) 612 (also referred to as central processing units, or CPUs) may be any known central processing unit, a processor, or a microprocessor. The CPU 612 may be coupled directly or indirectly to one or more computer-readable storage media (e.g., memory) 614. The memory 614 may include random access memory (RAM), read only memory (ROM), disk drive, tape drive, etc., or a combinations thereof. The memory 614 may be configured to store programs and data, including data structures. In some embodiments, the memory 614 may also include a frame buffer for storing data arrays.

In some embodiments, another computer system may assume the data analysis or other functions of the CPU 612. In response to commands received from an input device, the programs or data stored in the memory 614 may be archived in long term storage or may be further processed by the processor and presented on a display.

In some embodiments, the system 600 may include a communication interface 616 configured to conduct receiving and transmitting of data between other modules on the system and/or network. The communication interface 616 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the network.

In some embodiments, the system 610 may include an input/output interface 618 configured for receiving information from one or more input devices 620 (e.g., a keyboard, a mouse, and the like) and/or conveying information to one or more output devices 620 (e.g., a printer, a CD writer, a DVD writer, portable flash memory, etc.). In some embodiments, the one or more input devices 620 may be configured to control, for example, the generation of the management plan and/or prompt, the display of the management plan and/or prompt on a display, the printing of the management plan and/or prompt by a printer interface, the transmission of a management plan and/or prompt, among other things.

In some embodiments, the disclosed methods (e.g., FIGS. 2-5) may be implemented using software applications that are stored in a memory and executed by a processor (e.g., CPU) provided on the system 100. In some embodiments, the disclosed methods may be implemented using software applications that are stored in memories and executed by CPUs distributed across the system.

As such, any of the systems and/or modules of the system 100 may be a general purpose computer system, such as system 600, that becomes a specific purpose computer system when executing the routines and methods of the disclosure. The systems and/or modules of the system 100 may also include an operating system and micro instruction code. The various processes and functions described herein may either be part of the micro instruction code or part of the application program or routine (or combination thereof) that is executed via the operating system.

If written in a programming language conforming to a recognized standard, sequences of instructions designed to implement the methods may be compiled for execution on a variety of hardware systems and for interface to a variety of operating systems. In addition, embodiments are not described with reference to any particular programming language. It will be appreciated that a variety of programming languages may be used to implement embodiments of the disclosure. An example of hardware for performing the described functions is shown in FIGS. 1 and 6. It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A computer-implemented method of determining hemodynamic information for a patient, the method comprising:

receiving medical image data of the patient acquired by a medical image acquisition device, the medical image data including representations of tissue and blood of one or more arterial segments and surrounding area and being characterized through voxels of varying gray scale;

generating a geometrical representation of the one or more arterial segments from the medical image data, wherein a resulting geometrical representation is a three-dimensional model of a spatial volume of the lumens of one or more arterial segments;

determining boundaries and geometry data for each arterial lumen segment, the boundaries of which include a luminal volume and an inflow boundary of the luminal volume for each arterial segment, one or more outflow boundaries, and additional outflow boundaries that each represent a branch or bifurcation in the one or more arterial segments and are disposed between the inflow boundary and a first outflow boundary of the one or more outflow boundaries, the inflow boundary and the one or more outflow boundaries corresponding to a luminal cross-section of the each arterial segment, and the geometry data including a radius for the inflow boundary and a radius for each outflow boundary;

determining boundary conditions for the geometrical representation using the three-dimensional model, the boundary conditions including an interface between the luminal volume and arterial walls, an inflow boundary condition for the inflow boundary based on empirical parameters optimized for determination of a selected hemodynamic parameter of diagnostic interest, and an outflow boundary condition for each outflow boundary, the outflow boundary condition for each outflow boundary being determined using an outflow distribution parameter, the outflow distribution parameter being determined using the geometry data for one or more of the one or more outflow boundaries, the additional outflow boundaries, stored hemodynamic data, or a combination thereof, and a final outflow rate distribution among the outflow boundaries of the segments being determined using a minimization of outflow energy approach encompassing all outflow boundaries;

determining a patient-specific flow field for each arterial segment using a meshing technique within the geometrical representation, and incorporating all of the boundary conditions, the determining including updating outflow distribution boundary conditions as numerical iterations proceed to convergence;

determining hemodynamic information from the flow field, including pressures, velocities and wall shear stresses within the luminal volume and diagnostic hemodynamic indices, including fractional flow reserve, resting pressure ratios, or forces acting on arterial plaques; and providing an interactive display output of the hemodynamic information that enables receipt of user inputs to manipulate arterial segments, query pressure ratios within the segments, edit vessel segmentation, and assess diagnostic information associated with the hemodynamic information.

2. The method according to claim 1, wherein:
the one or more arterial segments correspond to the one or more coronary arterial segments.

3. The method according to claim 1, wherein:
the outflow distribution parameter is determined using a ratio of a radius for the first outflow boundary and a radius for a second outflow boundary, and the stored hemodynamic data; and the stored hemodynamic data defines an empirical relationship between (i) the ratio of the radius of the first outflow boundary and the radius of the second outflow boundary and (ii) a ratio of an outflow boundary condition for the first outflow boundary and an outflow boundary condition for the second outflow boundary.

4. The method according to claim 3, wherein:
the one or more outflow boundaries includes additional outflow boundaries disposed between the inflow boundary and the first outflow boundary; and
the outflow distribution parameter is used to determine an outflow boundary condition for the first outflow boundary, the second outflow boundary, and each additional outflow boundary.

5. The method according to claim 1, wherein:
the geometrical representation of the one or more arterial segments is discretized into a three-dimensional volumetric mesh; and
the geometrical representation includes a surface mesh representing a boundary of a vessel wall of each segment.

6. The method according to claim 1, wherein the flow field is determined using only the geometrical representation, the geometrical data and the boundary conditions.

7. The method according to claim 1, wherein the medical image data is computed tomography image data of the patient.

8. The method according to claim 1, wherein the hemodynamic information includes fractional flow reserve (FFR), instantaneous wave-free ratio (iFR), wall shear stress (WSS), axial plaque stress (APS), hyperemic and resting diastolic pressure (Pd)/aortic pressure (Pa) indexes, pressure indices over a range of physiologic states, or a combination thereof.

9. The method according to claim 1 further comprising:
receiving information regarding a position of a virtual stent disposed along one or more of the segments of the geometrical representation; and
updating the display output of the hemodynamic information.

10. A system for determining hemodynamic information for a patient, the system comprising:
at least one processor; and
a memory, wherein the processor is configured to cause:
obtaining medical image data of the patient acquired by a medical image acquisition device, the medical image data including representations of tissue and blood of one or more arterial segments and surrounding area and being characterized through voxels of varying gray scale;
generating a geometrical representation of the one or more arterial segments from the medical image data, wherein a resulting geometrical representation is a three-dimensional model of a spatial volume of the one or more arterial segments;
determining boundaries and geometry data for each arterial lumen segment, the boundaries of which include a luminal volume and an inflow boundary of the luminal volume for each arterial segment, one or more outflow boundaries, and additional outflow boundaries that each represent a branch or bifurcation in the one or more arterial segments and are disposed between the inflow boundary and a first outflow boundary of the one or more outflow boundaries; the inflow boundary and the one or more outflow boundaries corresponding to a luminal cross-section of each arterial segment; the geometry data including a radius for the inflow boundary and for each outflow boundary;
determining boundary conditions for the geometrical representation using the three-dimensional model, the boundary conditions including an interface between the luminal volume and arterial walls, an inflow boundary condition for the inflow boundary based on empirical parameters optimized for determination of a selected hemodynamic parameter of diagnostic interest, and an outflow boundary condition for each outflow boundary, the outflow boundary condition for each outflow boundary being determined using an outflow distribution parameter, the outflow distribution parameter being determined using the geometry data for one or more of the one or more outflow boundaries, the additional outflow boundaries, stored hemodynamic data, or a combination thereof, and a final outflow rate distribution among the outflow boundaries of the segments being determined using a minimization of outflow energy approach encompassing all outflow boundaries;
determining a patient-specific flow field for each arterial segment using a meshing technique within the geometrical representation, and incorporating all of the boundary conditions, the determining including updating outflow distribution boundary conditions as numerical iterations proceed to convergence;
determining hemodynamic information from the flow field including pressures, velocities and wall shear stresses within the luminal volume and diagnostic hemodynamic indices, including fractional flow reserve, resting pressure ratios, or forces acting on arterial plaques; and
providing an interactive display output of the hemodynamic information that enables receipt of user inputs to manipulate arterial segments, query pressure ratios within the segments, edit vessel segmentation, and assess diagnostic information associated with the hemodynamic information.

11. The system according to claim 10, wherein:
the one or more arterial segments corresponds to the one or more coronary arterial segments.

12. The system according to claim 10, wherein:
the outflow distribution parameter is determined using a ratio of a radius for the first outflow boundary and a radius for the second outflow boundary and the stored hemodynamic data; and
the stored hemodynamic data defines an empirical relationship between (i) the ratio of the radius of the first outflow boundary and the radius of the second outflow boundary and (ii) a ratio of the outflow boundary condition for the first outflow boundary and the outflow boundary condition for second outflow boundary.

13. The system according to claim 12, wherein:
the one or more outflow boundaries includes additional outflow boundaries disposed between the inflow boundary and the first outflow boundary; and
the outflow distribution parameter is used to determine an outflow boundary condition for the first outflow boundary, the second outflow boundary, and each additional outflow boundary.

14. The system according to claim 10, wherein:
the geometrical representation of the one or more arterial segments is discretized into a three-dimensional volumetric mesh; and the geometrical representation includes a surface mesh representing a boundary of a vessel wall of each segment.

15. The system according to claim 10, wherein the flow field is determined using only the geometrical representation, the geometrical data and the boundary conditions.

16. The system according to claim 10, wherein the medical image data is computed tomography image data of the patient.

17. The system according to claim 10, wherein the hemodynamic information includes fractional flow reserve (FFR), instantaneous wave-free ratio (iFR), wall shear stress (WSS), axial plaque stress (APS), hyperemic and resting diastolic pressure (Pd)/aortic pressure (Pa) indexes, pressure indices over a range of physiologic states, or a combination thereof.

18. The system of according to claim 10, wherein information regarding a position of a virtual stent disposed along one or more of the segments of the geometrical representation is received, and wherein the display output of the hemodynamic information is updated in accordance with the information.

19. A computer-implemented method of determining boundary conditions for a geometrical representation of an arterial anatomy of a patient, the method comprising:

receiving medical image data of the patient acquired by a medical image acquisition device, the medical image data including representations of tissue and blood of one or more arterial segments and surrounding area and being characterized through voxels of varying gray scale;

generating a geometrical representation of the one or more arterial segments from the medical image data, wherein a resulting geometrical representation is a three-dimensional model of a spatial volume of the lumens of one or more arterial segments;

determining boundaries and geometry data for each arterial lumen segment using the three-dimensional model, the boundaries of which include an inflow boundary of the luminal volume for each arterial segment and one or more outflow boundaries, the inflow boundary and the one or more outflow boundaries corresponding to a luminal cross-section of the each arterial segment, the one or more outflow boundaries including a first outflow boundary and a second outflow boundary, the second outflow boundary representing a branch or bifurcation in the one or more arterial segments and being disposed between the first outflow boundary and the inflow boundary, the geometry data including a radius for the inflow boundary and for each outflow boundary;

determining an outflow distribution parameter using the geometry data for one or more of the one or more outflow boundaries and stored hemodynamic data, the hemodynamic data defining an empirical relationship between (i) the ratio of the radius of the first outflow boundary and the radius of the second outflow boundary and (ii) a ratio of the outflow boundary condition for the first outflow boundary and the outflow boundary condition for second outflow boundary; and a final outflow rate distribution among the outflow boundaries of the segments being determined using a minimization of outflow energy approach encompassing all outflow boundaries;

determining an outflow boundary condition for each outflow boundary using the outflow distribution parameter and the inflow boundary; and providing an interactive display output of the geometrical representation that enables receipt of user inputs to manipulate arterial segments, query pressure ratios within the segments, and edit vessel segmentation.

20. The method according to claim 19, wherein:

the outflow distribution parameter is determined using a ratio of a radius for the first outflow boundary and the second outflow boundary and the stored hemodynamic data; and the one or more outflow boundaries include additional outflow boundaries disposed between the inflow boundary and the first outflow boundary.

* * * * *